United States Patent [19]

Alexandrov et al.

[11] Patent Number: 4,954,253

[45] Date of Patent: Sep. 4, 1990

[54] DEVICE FOR PREPARING A GRADIENT SOLUTION FOR A HIGH-PRESSURE LIQUID CHROMATOGRAPH

[75] Inventors: Maxim L. Alexandrov; Vsevolod V. Shevkunov; Alexandr J. Pavlov, all of Leningrad, U.S.S.R.

[73] Assignee: Nauchno-Tekhnicheskoe Objedinenie Akademii Nauk SSSR, Leningrad, U.S.S.R.

[21] Appl. No.: 390,702

[22] Filed: Aug. 7, 1989

Related U.S. Application Data

[63] Continuation of Ser. No. 332,932, filed as PCT SU87/00054 on May 14, 1987, abandoned, which is a continuation of Ser. No. 307,309, Jan. 23, 1989, abandoned.

[51] Int. Cl.$^5$ .............................................. B01D 15/08
[52] U.S. Cl. .................................. 210/198.2; 210/101; 366/160; 366/177
[58] Field of Search ................... 366/152, 160, 177; 210/101, 198.2; 55/386

[56] References Cited

U.S. PATENT DOCUMENTS

| | | | |
|---|---|---|---|
| 3,712,513 | 1/1973 | Ashmead et al. | 222/134 |
| 4,389,316 | 6/1983 | Falk | 210/198.2 |
| 4,437,812 | 3/1984 | Abu-Shumays et al. | 210/198.2 |
| 4,448,684 | 5/1984 | Paradis | 210/198.2 |
| 4,475,821 | 10/1984 | Koch | 210/198.2 |
| 4,478,713 | 10/1984 | Girot | 210/198.2 |
| 4,541,452 | 9/1985 | Paradis | 210/198.2 |
| 4,591,442 | 5/1986 | Andrews | 210/198.2 |
| 4,595,496 | 6/1986 | Carson | 210/101 |
| 4,714,545 | 12/1987 | Bente | 210/101 |
| 4,728,434 | 3/1988 | Trafford | 210/198.2 |

FOREIGN PATENT DOCUMENTS

| | | | |
|---|---|---|---|
| 652916 | 3/1979 | U.S.S.R. | 210/198.2 |
| 686640 | 9/1979 | U.S.S.R. | 210/198.2 |
| 1000907 | 2/1983 | U.S.S.R. | 210/198.2 |

*Primary Examiner*—Ernest G. Therkorn
*Attorney, Agent, or Firm*—Ladas & Parry

[57] ABSTRACT

A device for preparing a gradient solution for a high-pressure liquid chromatograph comprises vessels (1) containing eluents, a switch-over unit (7), a piston pump (9) and a mixer (4). Each vessel (1) containing eluents has a movable partition (10) dividing it into two chambers (11,12). The switch-over unit (7) is fashioned as a flow-through chamber (13) accommodating a rotary switch-over valve having a rotor (15) and stator (16). The rotor (15) has one through passage (17), whereas the stator (16) is provided with through passages (18) equal in number to the number of vessels (1) each communicating with the corresponding vessel (1) and arranged so that during rotation of the rotor (15) the through passage (17) provided therein is capable of connecting alternately to the passages (18) of the stator (16).

2 Claims, 2 Drawing Sheets

DEVICE FOR PREPARING A GRADIENT SOLUTION FOR A HIGH-PRESSURE LIQUID CHROMATOGRAPH

This is a continuation of application Ser. No. 7/307,309 filed on Jan. 23, 1989, now abandoned, which is a continuation of U.S. Ser. No. 332,932, filed as PCT SU87/00054 on May 14, 1987, now abandoned.

FIELD OF THE INVENTION

This invention relates generally to equipment associated with physical and chemical chromatographic analysis of complex mixtures, and more particularly concerns devices for preparing a gradient solution for high-pressue liquid chromatographs.

BACKGROUND OF THE INVENTION

There is known a device for preparing a gradient solution for a high-pressure liquid chromatograph comprising vessels containing eluents of various compositions communicating by way of pipes through a switch-over unit with displacement chambers of ram-type pumps and through a mixer with the inlet of the chromatographic column (U.S. Pat. No. 3,712,513).

In this known device the number of pumps is dictated by the number of components in the gradient eluting solution; each such pump delivering under pressure the respective component at a rate determined by a control computer. The computer also issues signals to solenoid-operated cut-off values in the switch-over unit.

However, this prior art device fails to sufficiently accurately reproduce the shape of the gradient curve due to the low frequency of actuation of the solenoid-operated valves sealed to withstand the high working pressure of the chromatograph. Another disadvantage is that such a thorough sealing affects the reliability and shortens the service life of the valves.

Also, the aforedescribed device is not applicable for preparing a gradient solution for microcolumn chromatographs. The entire volume of the gradient solution required for carrying out complete analysis in the microcolumn chromatograph amounts to approximately 20–60 mkl, whereas the volume of the displacement chamber of the ram-type pump is never less than 30–80 mkl. At the same time, it is impossible to prepare a gradient solution characterized by a curve of intricate shape by one or two strokes of the pump.

There is also known a device for preparing a gradient solution for a high-pressure liquid chromatograph comprising vessels containing eluents communicating by pipes through a switch-over unit with the displacement chamber of a piston pump and through a mixer with the inlet of the chromatographic column (c.f., U.S. Pat. No. 4,437,812).

This device includes only one pump the displacement chamber of which also functions as a mixer. The switch-over unit comprises distribution valves to proportion the components of the gradient solution, and two cut-off valves acting to either separate the chromatographic column from the pump at the stage of preparation of the gradient solution, or to separate the pump from the proportioning valves at the point of forcing the mixture to the chromatographic column. The proportioning valves are sealed to withstand low pressure, since they are actuated only during the suction cycle of the pump, the cut-off valves being capable of withstanding high pressure.

The proportioning valves in this prior art device are sufficiently fast-acting; however, the frequency of reciprocations of the ram-type pump is rather limited, and fails to ensure a sufficiently accurate reproduction of a set shape of the gradient curve.

As the previously described device, this apparatus is not applicable for use in microcolumn chromatographs due to the substantial volume of the displacement chamber of the piston pump.

SUMMARY OF THE INVENTION

The present invention aims at providing an apparatus for preparing a gradient solution for a high-pressure liquid chromatograph having such a switch-over system as to enable feeding the gradient solution to the column of the liquid chromatograph by any small quantities or even feeding the solution continuously by a single pump.

The aims of the invention are attained by that in a device for preparing a gradient solution for a high-pressure liquid chromatograph comprising vessels containing eluents communicating by way of pipes through a switch-over unit with a displacement chamber of a piston-type pump and through a mixer with the inlet of a chromatographic column, according to the invention, each of the eluent-containing vessels is provided with a movable partition dividing the interior of the vessel into two chambers, particularly, a first chamber communicating with the mixer and filled with an eluent, and a second chamber filled with an inert liquid and communicating with the switch-over unit fashioned as a flow-through chamber arranged between outlets of the pipes and displacement chamber of the piston-type pump, and a rotable switch-over valve disposed inside the flow-through chamber and having a rotor and a stator, the rotor having one through passage communicating with the interior of the flow-through chamber, the stator having through passages equal in number to the number of eluent-containing vessels, each communicating with the corresponding vessel and arranged so that during rotation of the rotor the through passage provided therein can alternately connect to the passages of the stator.

For ensuring a more accurate operation it is advisable that the device be provided with additional eluent-containing vessels similar to the main vessels, and an additional stator of the switch-over valve similar to the main stator, adpated for cooperation with the rotor simultaneously with the main stator, and having through passages equal in number to the number of additional vessels and each connected to the corresponding additional eluent-containing vessel, the sequence of arrangement of the through passages in the additional stator being the reverse of the sequence of arrangement of the through passages in the main stator.

The device for preparing a gradient solution for a high-pressure liquid chromatograph embodying the present invention makes it possible to reduce the volume of portions of liquid delivered from each separate eluent-containing vessel, in this case dictated entirely by the frequency of action of the switch-over valve operating under a lighter duty through accommodating it in an inert lubricating liquid and dispensing with pressure-sealing this valve. This in turn ensures a more accurate reproducibility of the shape of the gradient curve providing a more efficient and precise chromatographic analysis. Such an arrangement of the device allows to use it in microcolumn liquid chromatographs, where the quantity of eluent necessary for analysis is in the order of tens of microliters.

In the device according to the invention the corrosive eluting liquids are separated from the important rubbing and rotating parts in the valves and pumps of the chromatograph resulting in increased service life and higher reliability of the chromatograph.

BRIEF DESCRIPTION OF THE DRAWINGS

The device according to the invention is structurally simple, especially in the case when it is necessary to use multicomponent gradient solutions, thanks to dispensing with a plurality of valves.

BEST MODE OF CARRYING OUT THE INVENTION

Figure 1:
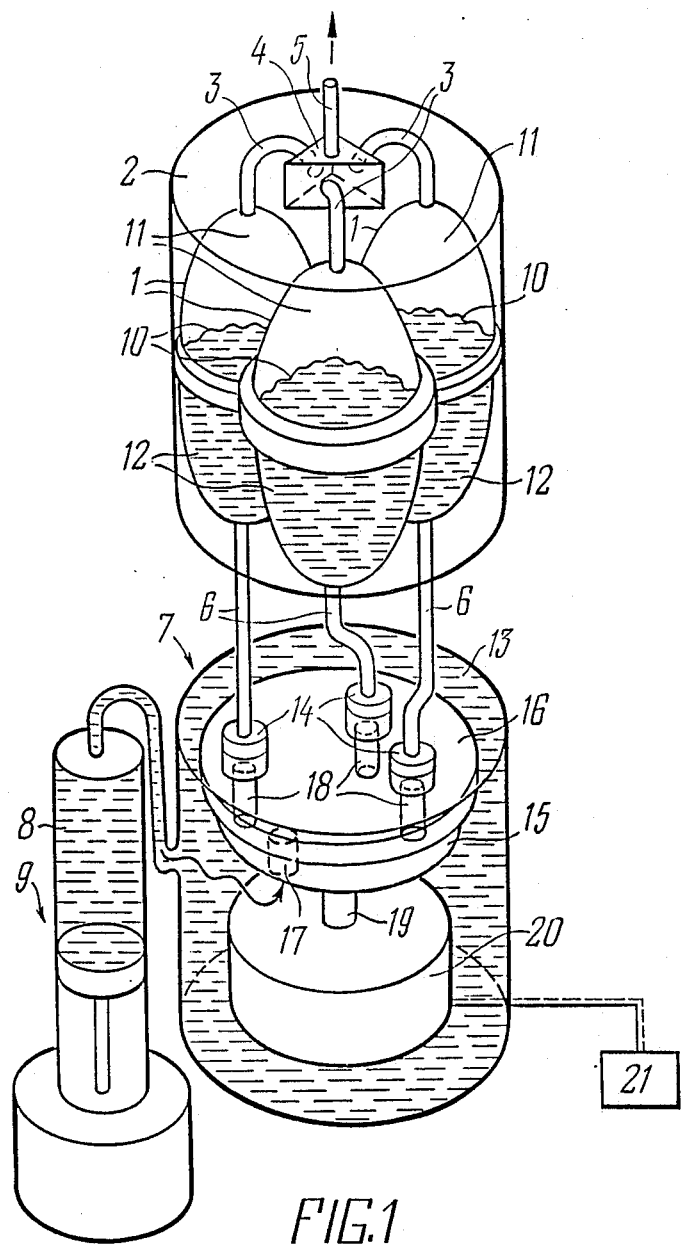
FIG. 1 is an isometric view of a device for preparing a gradient solution for a high-pressure liquid chromatograph.

A device for preparing a gradient solution for a high pressure liquid chromatograph with reference to FIG. 1 comprises vessels 1 containing eluents and enclosed in a protective casing 2; these vessels 1 communicating by way of pipes 3 with a mixer 4 having an outlet 5 connectable to the inlet of a chromatographic column (not shown). The vessels 1 containing the eluents also communicate by way of pipes 6 and through a switch-over unit 7 with a displacement chamber 8 of a piston pump (such as a syringe-type pump). Each vessel 1 is provided with a movable partition 10 dividing the interior of the vessel 1 into two chambers 11, 12, of which the first such chamber 11 communicates with the mixer 4 and contains the eluent, whereas the second chamber 12 contains an inert liquid and communicates by way of the pipe 6 with the switch-over unit 7. The switch-over unit 7 has the form of a hermetically sealed flow-through chamber 13 containing the inert liquid and disposed between outlets 14 of the pipes 6 and the displacement chamber 8 of the piston pump 9, and a rotary switch-over valve arranged inside the flow-through chamber 13 and having a rotor 15 and a stator 16. The rotor 15 has one through passage 17 communicating with the interior of the flow-through chamber 13. The stator 16 has through passages 18 equal in number to the number of vessels 1 containing the eluents each communicating by way of its own pipe 6 with the respective vessel 1 and disposed so that during rotation of the rotor 15 the through passage 17 of the rotor can alternately be connected to the passages 18 of the stator 16. The rotor 15 of the switch-over valve is secured on a shaft 19 of a step electric motor 20 electrically connected to a control computer 21.

Figure 2:
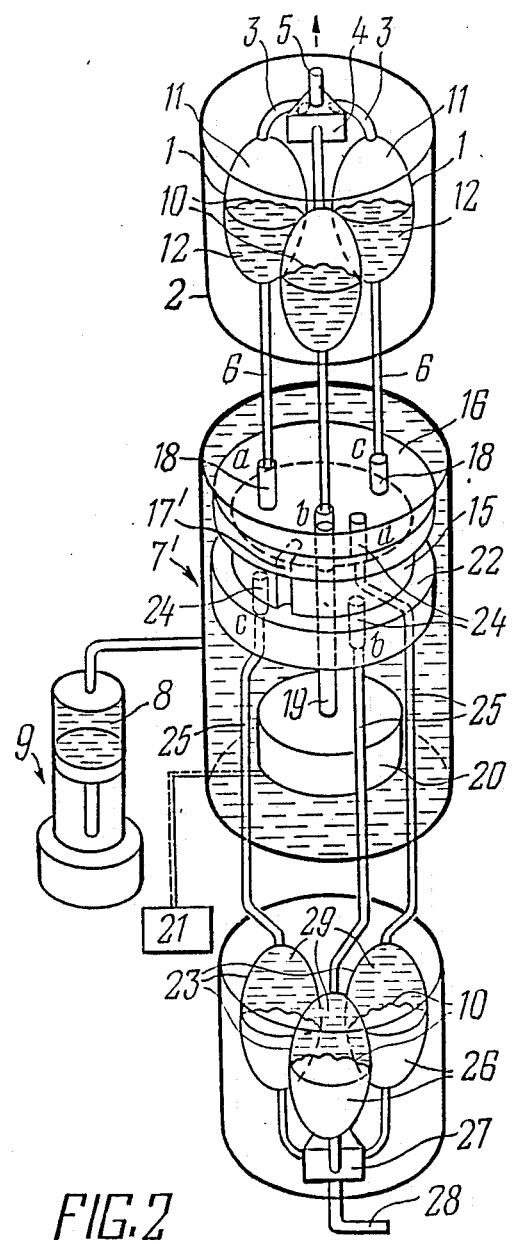
FIG. 2 is an isometric view of a modified form of the proposed device having additional eluent-containing vessels and an additional stator.

In an alternative embodiment of the proposed device shown in FIG. 2, as distinct from the heretofore described modification, it comprises an additional stator 22 of the switch-over valve substantially similar to the main stator 16 adapted for cooperation with the rotor 15 and simultaneously with the main stator 16, and additional vessels 23 containing eluents. The stator 22 has its own through passages 24 equal in number to the number of the additional vessels 23. The passages 24 are connected by way of additional pipes 25 with the corresponding vessels 23. The additional vessels 23 are similar to the main vessels 1; components of the eluting gradient solution in the chambers 26 of the additional vessels 23 are similar to the solutions present in the chambers 11 of the main vessels 1; however, the sequence of arrangement of the through passages 24 in the additional stator 2 (c, b, a) is the reverse of the arrangement of the through passages 18 in the main stator 16 (a, b, c).

The chambers 16 of the vessels 23 are connected to an additional mixer 27 having an outlet 28 intended for connection, for example, to a comparison chamber of a detector (not shown). The through passage 17 in this modification of the device has the form of a recess in the rotor 15.

The device for preparing a gradient solution for a high pressure liquid chromatograph with reference to FIG. 1 operates in the following manner.

The piston 9 acts to continuously supply the inert liquid under high pressure from the displacement chamber 8 to the hermetically sealed flow-through chamber 13, wherefrom the noncompressible lubricating inert liquid flows through the switch-over unit 7 along the pipes 6 to the bottom chambers 12 of the vessels 1 containing components of the eluting gradient solution and acts on the movable partitions 10 to move them and force set proportions of the eluents from the top chambers 11 along the pipes 3 to the mixer 4, from which the prepared and mixed gradient solution is delivered through the outlet 5 to the chromatographic column.

The switch-over valve of the unit 7 is rotated by the step motor 20 the shaft 19 of which has mounted thereon the rotor 15 with the through passage 17. The step motor 20 is, in turn, controlled by signals produced by the control computer 21. As the rotor 15 is turned a preset angle, the through passage 17 is registered for a certain period in line with one of the through passages 18 provided in the stator 16 of the switch-over valve, and the inert liquid flows from the hermetically sealed flow-through chamber 13 to the corresponding pipe 6 connected by its outlet to the passage 18 of the stator 16. Accordingly, the same quantity of the eluent contained in the vessel 1 to which this pipe is connected will be forced to the mixer 4. In order to avoid fluctiations of pressure, time spaces between switch-overs of the passages 18 in the stator 16 are minimized to milliseconds or even still shorter, which entails high frequency of such switch-overs. Each set magnitude of the concentration of the components of the gradient solution in the mixer 4 is attained by a multitude of connections of the passages 18 of the stator 16 to the flow-through chamber 13 while executing the movement of the rotor 15 according to the program calculated by the computer 21. The number of communications of the passage 17 of the rotor 15 with each passage 18 of the stator 16 per unit time and sequence of such communications varies, and is calculated by the computer 21 according to the set shape of the gradient curve. The stability in the number of connections of the passage 17 of the rotor 15 to all the passages 18 of the stator 16 per unit time is carefully maintained in order to ensure the preset volumetric supply of the gradient solution to the chromatographic column in accordance with the magnitude of volumetric feeding provided by the piston pump 9. Otherwise, a pressure difference may take place between the hermetically sealed flow-through chamber 13 and chambers 12 of the vessels 1.

During operation of the modified form of the proposed device with reference to FIG. 2, as distinct from one shown in FIG. 1, the passage 17 of the rotor 15 communicates simultaneously with one of the passages 18 of the stator 16 and with one of the passages 24 of the stator 22. Therewith, admitted to the corresponding chamber 12 of the vessels 1, as well as to the corresponding chamber 29 of the vessels 23, are equal portions of the inert liquid from the flow-through chamber 13 of the switch-over unit 7. As a result, portions of the corresponding component of the gradient solution (eluent) are forced to the mixers 4 and 27. By virtue of the fact that the sequence of arrangement of the passages 24 in the stator 22 is reverse to that of the passages 18 in the stator 16, the concentration of the gradient solution at the outlet 28 from the additional mixer 27 is characterized by a curve the shape of which is reverse (symmetrical relative to a line running parallel with the axis of abscissas and passing through the point at the axis of ordinates with the initial magnitude of concentration of the gradient solution) to the shape of the curve representing a concentration of the gradient solution at the outlet 5 from the mixer 4.

The use of the gradient solution obtainable at the outlet 28 of the device makes it possible to improve the accuracy of chromatographic analysis. For example, in the case when the gradient solution contains substances which facilitate the chromatographic process but hamper detection (such as optically-active substances), a second additional mixer (not shown) is preferably provided before the detector to mix the gradient solution from the outlet 5 of the device which has passed through the chromatographic column with the gradient solution of reverse distribution of components entering from the outlet 28 of the device. In the second additional mixer there is formed a stable concentration of substances hampering detection to result in a new background line in the detector. At the level of a continuous, although a higher, background the chromatographic peaks of the separated substances can be clearly visible.

A gradient solution with a time-reversed distribution of components obtained in the additional mixer 27 can, in the case of employment of a difference detector, be directed to a comparison tray of the detector, and the readings obtained in the comparison tray are subtracted from the readings obtained in the main tray. This procedure is advisable when using optical detection. In the case of electrochemical detection it is more preferable to use an additional gradient solution for suppressing the ionic activity of the eluent of this or that sign.

INDUSTRIAL APPLICABILITY

The device for feeding a gradient solution, to the column of a high-pressure liquid chromatograph is intended for carrying out chemical analyses in biochemistry, molecular biology and pharmaceutical industry.

We claim:

1. A device for preparing a gradient solution for a high-pressure liquid chromatograph comprising vessels (1) containing eluents communicating by way of pipes (6) through a switch-over unit (7) with a displacement chamber (8) of a piston-type pump (9) and through a mixer (4) with the inlet of a chromatographic column characterized in that each of the eluent-containing vessels (1) is provided with a movable partition (10) dividing the interior of the vessel (1) into two chambers (11,12), the chamber (11) communicating with the mixer (4) and filled with an eluent, whereas the chamber (12) is filled with an inert liquid and communicates with the switch-over unit (7) fashioned as a flow-through chamber (13) arranged between outlets (14) of the pipes (6) and displacement chamber (8) of the piston-type pump (9), and a rotatable switch-over valve disposed inside the flow-through chamber (13) of the rotatable valve having a rotor (15) and a stator (16), the rotor (15) having one through passage (17) communicating with the interior of the flow-through chamber (13), the stator (16) having through passages (18) equal in number to the number of eluent-containing vessels (1), each communicating through the pipe (6) with the corresponding vessel (1) and arranged so that during rotation of the rotor (15) the through passage (17) provided therein can alternately connect it to the passages (18) of the stator (16).

2. A device as claimed in claim 1, characterized in that it is provided with additional eluent-containing vessels (23) similar to the main vessels (1), and an additional stator (22) of the switch-over valve similar to the main stator (16) adapted for cooperation with the rotor simultaneously with the main stator (16) and having through passages (24) equal in number to the number of additional vessels (23) and connected to the corresponding vessel (23), the sequence of arrangement of the through passages (24) in the additional stator (22) being the reverse of the sequence of arrangement of the through passages (18) in the main stator (16).

* * * * *